United States Patent [19]

Botannet et al.

[11] Patent Number: 5,117,043

[45] Date of Patent: May 26, 1992

[54] PROCESS FOR THE PREPARATION OF N-SULFOMETHYLGLYCINATE

[75] Inventors: Bernard Botannet, Vienne; Jean-Louis Clavel, Ecully; Jean-Pierre Corbet, Ecully; Michel Mulhauser, Ecully, all of France

[73] Assignee: Rhone-Poulenc Agrochimie, Lyons, France

[21] Appl. No.: 388,570

[22] Filed: Aug. 1, 1989

[30] Foreign Application Priority Data

Aug. 18, 1988 [FR] France .................. 88 11141

[51] Int. Cl.$^5$ .................. C07C 303/326
[52] U.S. Cl. .................. 560/150; 71/86; 558/108; 558/172; 562/556
[58] Field of Search .......... 560/150, 149; 562/556

[56] References Cited

U.S. PATENT DOCUMENTS

| | | | |
|---|---|---|---|
| 3,799,758 | 3/1974 | Franz | 71/86 |
| 3,835,000 | 9/1974 | Frazier et al. | 204/78 |
| 3,868,407 | 2/1975 | Franz et al. | 71/86 X |
| 3,950,402 | 4/1976 | Franz | 71/86 X |
| 4,069,048 | 1/1978 | Tsubota et al. | 96/3 |
| 4,147,719 | 4/1979 | Franz | 544/78 X |

FOREIGN PATENT DOCUMENTS 0019384 11/1980 European Pat. Off. .

Primary Examiner—Jose G. Dees
Assistant Examiner—Vera C. Clarke
Attorney, Agent, or Firm—Morgan & Finnegan

[57] ABSTRACT

The invention relates to an N-sulfomethylglycinate of formula:

$$HO_3S-CH_2-NH-CH_2-COOR_1 \qquad (I)$$

$COOR_1$ being a hydrolysable carboxylic ester group.

It also relates to a process for the preparation of the compound of formula (I) consisting in putting in contact sulfur dioxide, formaldehyde, and glycine in the presence of a $R_1OH$ alcohol, or glycinate.

It also relates to the use of the compound of formula (I) for the preparation of herbicides of the glyphosate type of reaction with a phosphite or a phosphonate of formula $(R_2O)_2 P(O) H$ in which $(R_2O)_2 P$ is a hydrolysable phosphonic ester group, then optionally by a subsequent hydrolysis reaction.

20 Claims, No Drawings

PROCESS FOR THE PREPARATION OF N-SULFOMETHYLGLYCINATE

The present invention relates to N-sulfomethyl glycinate compounds, a process for the preparation of these compounds and the use of these compounds for the preparation of herbicides of the glyphosate type.

TECHNICAL CONTEXT

Glyphosate (N-phosphonomethylglycine) and its salts are wide-spectrum herbicides which are well known in the art. These herbicides and the processes for obtaining them are described, for example, in the following patents: U.S. Pat. No. 3,799,758; U.S. Pat. No. 3,835,000; U.S. Pat. No. 3,868,407; U.S. Pat. No. 3,950,402; U.S. Pat. No. 4,083,893; U.S. Pat. No. 4,147,719 and EP-A-0,019,384. Furthermore, the compound N-sulfomethylglycine is known from U.S. Pat. No. 4,069,048.

SUBJECT OF THE INVENTION

The subject of the invention is to suggest a way of arriving at the glyphosate-type herbicides which has numerous advantages: economy, restricted number of stages, excellent yields and ease of development to the industrial scale.

THE INVENTION

Firstly the invention relates to a N-sulfomethyl glycinate of formula:

$$HO_3S-CH_2-NH-CH_2-COOR_1 \quad (I)$$

in which formula: $COOR_1$ is a hydrolyzable carboxylic ester group.

Hydrolyzable groups are well known in the art. Within the scope of the present invention, a hydrolyzable $COOR_1$ group is understood to mean all the groups which can be lyzed in the presence of water, optionally in an acid or basic medium, to give the corresponding $-COOH$ acid and $R_1OH$ alcohol.

A hydrolyzable $COOR_1$ group is understood to mean a group in which the $R_1$ radical is in particular chosen from the following radicals:
linear or branched $C_1-C_{18}$ alkyl, preferably $C_1-C_{12}$
linear or branched $C_2-C_{18}$ alkenyl, preferably $C_2-C_{12}$
linear or branched $C_2-C_{18}$ alkynyl, preferably $C_2-C_{12}$
linear or branched $C_3-C_{18}$ cycloalkyl, preferably $C_3-C_{12}$
linear or branched $C_6-C_{14}$ aryl, preferably $C_6-C_{10}$
linear or branched $C_7-C_{15}$ aralkyl, preferably $C_7-C_{11}$,
these radicals being optionally substituted with one or more halogen atoms or $C_1-C_6$ alkoxy or alkylthio radicals, the aryl or aralkyl radicals being capable, in addition, of comprising 1 to 4 hetero atoms chosen from the atoms of oxygen, sulfur and nitrogen (for example furyl, thiophenyl or pyridyl).

Even more preferably, $R_1$ is chosen from the $C_1-C_6$ alkyl or $C_6-C_{10}$ aryl or $C_7-C_{11}$ aralkyl groups, the said radicals being optionally substituted with one or more halogen atoms or $C_1-C_6$ alkoxy radicals.

In the present specification the formulae of chemical compounds are represented in the nonionic form. It is nevertheless clear to those versed in the technique that in the case of the amino acids, such as, for example the compound of formula (I) these can exist in the zwitterionic form.

PREPARATION PROCESS

One preparation process consists in putting formaldehyde, sulfur dioxide and a glycinate of formula: $H_2N-CH_2-COOR_1$ in contact.

The reaction is preferably carried out with the following molar proportions:

| | |
|---|---|
| glycinate | 1 mole |
| sulfur dioxide | 0.95 mole to saturation |
| formaldehyde | 0.95 to 3 moles | but preferably in a proportion greater than that of the glycinate (1.5 to 2.5 moles).

The reaction is generally carried out between 0° and 100° C., preferably between 10° C. and 90° C., by simply mixing the reactants.

The formaldehyde is used in one or another easily accessible forms. According to the most usual form it is used in the form of an aqueous solution of concentration between 1% and saturation, preferably from 30 to 40%.

The reaction may be carried out in the presence of an inert solvent; sometimes such a solvent is useless because the reaction medium normally contains water, particularly as a result of the use of formaldehyde in aqueous solution.

In the case in which formaldehyde is used in a nonaqueous form, a multitude of solvents, alone or in mixtures, may be used.

Among the aprotic solvents, saturated aliphatic hydrocarbons such as n-pentane, isopentane, 2-methylhexane and 2,2,5-trimethylhexane, aromatic hydrocarbons such as benzene, toluene, xylene and ethylbenzene, saturated aliphatic ethers such as tetrahydrofuran and isopentylether, aromatic ethers such as benzylethyl ether, saturated aliphatic or aromatic ketones such as methyl ethyl ketone, methylisobutyl ketone and acetophenone, saturated aliphatic or aromatic halogenated hydrocarbons such as fluorobenzene, 1-chloro-2-methylpropane and isobutyl chloride, and saturated aliphatic or aromatic esters such as isobutyl isobutyrate, ethyl acetate and methyl benzoate may be mentioned. All these solvents may be present alone or as a mixture.

Among the protic solvents the saturated aliphatic or aromatic alcohols such as methanol, ethanol, isopropanol and phenol, and saturated aliphatic or aromatic acids such as acetic acid and benzoic acid may be mentioned.

Another particularly advantageous and unexpected preparation process consists in reacting formaldehyde, sulfur dioxide, an alcohol of the formula R OH and glycine of formula $H_2N-CH_2-COOH$.

The reaction is preferably carried out with the following molar proportions:

| | |
|---|---|
| glycine | 1 mole |
| sulfur dioxide | 0.95 mole to saturation |
| formaldehyde | 0.95 to 3 moles | but preferably in a proportion greater than that of the glycinate (1.5 to 2.5 moles).

 greater than 0.95 mole but preferably in a proportion greater than that of the glycinate (greater than 1.2 moles), advantageously greater than 1.5 moles, and very advantageously greater than 1.8 moles.

According to an advantageous form of the invention the $R_1OH$ alcohol will be used as solvent, the other aprotic solvents mentioned above being capable of being used, optionally, as cosolvents. Preferably, ethanol will be chosen as solvent.

The reaction is, otherwise, carried out in the same conditions as above.

This last process is particularly preferred, and moreover absolutely unexpected, since it leads to the N-sulfomethylglycinate with a practically quantitative yield.

The subject of the invention is also the use of compounds of formula (I) in the preparation of known herbicides of the glyphosate type, the use consisting in putting the compound of formula (I) in contact with a phosphite of formula:

$$(R_2O)_2 PH \quad (II)$$

$(R_2O)_2P(O)$ being a hydrolyzable phosphonic ester group in order to arrive at the compound of formula:

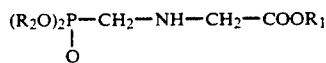 (III)

These hydrolyzable groups are well known to those versed in the technique. A hydrolyzable $(R_2O)_2P(O)$ group is understood to mean a group which, under the action of water, optionally in an acid or basic medium, is lyzed to an alcohol $R_2OH$ and an acid $(O)P(OH)_2$.

A hydrolyzable $(R_2O)_2P(O)$ group is understood to mean a group the $R_2$ radical of which is in particular chosen from the following radicals:
linear or branched $C_1$-$C_{18}$ alkyl, preferably $C_1$-$C_{12}$
linear or branched $C_2$-$C_{18}$ alkenyl, preferably $C_2$-$C_{12}$
linear or branched $C_2$-$C_{18}$ alkynyl, preferably $C_2$-$C_{12}$
linear or branched $C_3$-$C_{18}$ cycloalkyl, preferably $C_3$-$C_{12}$
linear or branched $C_6$-$C_{14}$ aryl, preferably $C_6$-$C_{10}$
linear or branched $C_7$-$C_{15}$ aralkyl, preferably $C_7$-$C_{11}$, these radicals being optionally substituted with one or more halogen atoms or $C_1$-$C_6$ alkoxy or alkylthio radicals, the aryl or aralkyl radicals being capable, in addition, of comprising 1 to 4 hetero atoms chosen from the atoms of oxygen, sulfur and nitrogen (for example furyl, pyridyl and thiophenyl).

Even more preferably, $R_2$ is chosen from the $C_1$-$C_6$ alkyl or $C_6$-$C_{10}$ aryl or $C_7$-$C_{11}$ aralkyl groups, the said radicals being optionally substituted with one or more halogen atoms or $C_1$-$C_6$ alkoxy radicals.

The reaction is carried out in the bulk phase or in an inert solvent.

Among the aprotic solvents, saturated aliphatic hydrocarbons such as n-pentane, isopentane, 2-methylhexane and 2,2,5-trimethylhexane, aromatic hydrocarbons such as benzene, toluene, xylene and ethylbenzene, saturated aliphatic ethers such as tetrahydrofuran and isopentylether, aromatic ethers such as benzylethyl ether, saturated aliphatic or aromatic ketones such as methyl ethyl ketone, methylisobutyl ketone and acetophenone, saturated aliphatic or aromatic halogenated hydrocarbons such as fluorobenzene, 1-chloro-2-methylpropane and isobutyl chloride, and saturated aliphatic or aromatic esters such as isobutyl isobutyrate, ethyl acetate and methyl benzoate may be mentioned. All these solvents may be present alone or as a mixture.

Among the protic solvents the saturated aliphatic or aromatic alcohols such as methanol, isopropanol and phenol and the saturated aliphatic or aromatic acids such as acetic acid and benzoic acid may be mentioned.

The reaction temperature is between 50° C. and 250° C. or the boiling point of the solvent, and preferably 100° to 200° C.

Although a large excess (3/1 to ⅓ in molar ratios) of one of the reactants with respect to the other is possible, it is more advantageous in practice not to diverge from the stoichiometry by more than 20%.

The compound of formula (III) is a product which is known from the document EP 0,135,454. It may be hydrolyzed in a known manner to arrive at the N-phosphonomethylglycine or glyphosate herbicide.

The following examples illustrate the invention:

Glycine (7.5 g; 100 millimoles), 95% ethanol (120 cc) and a 31.5% aqueous solution of formaldehyde (19 g; 200 millimoles) are introduced successively into a two-necked flask provided with an alcohol thermometer. The suspension obtained is saturated with $SO_2$ until it has completely dissolved (increase of the temperature to 45° C.). After 1 h 30 min stirring at ambient temperature a precipitate starts to appear. Stirring is maintained for a further 3 h and the precipitate is filtered and washed with ethanol (30 cc) and then ether (30 cc). After drying ethyl sulfomethylglycinate (18.8 g) is obtained in a purity greater than 95% (determined by NMR at 360 MHz): this is a 95.5% yield with respect to the starting glycine.

m.p. (Kofler) = 154° C.

Ethyl sulfomethylglycinate (2.46 g; 12.5 millimoles), xylene (20 cc) and diisopropyl phosphite (2.07 g; 12.5 mmol) are introduced successively into a two-necked flask provided with a thermometer and a means of cooling. The suspension is heated for 1 h at 105° C., and after evaporation of the solvent under a vacuum provided by a water-jet pump an orange oil (3.81 g) is recovered, which is shown by titration to contain 40% protected glyphosate.

We claim:

1. A process for preparing a N-sulfomethylglycinate having the formula $HO_3S-CH_2-NH-CH_2-COOR_1$ (I), which comprises the step of reacting, at between 0° C. and 100° C., 0.95 to 3 moles of formaldehyde, 0.95 moles to saturation of sulfur dioxide, and 1 mole of a glycinate having the formula $H_2N-N-CH_2-COOR_1$ (II), where in both formulas I and II the $R_1$ is a linear or branched $C_1$-$C_6$ alkyl, $C_3$-$C_{12}$ cycloalkyl, $C_6$-$C_{10}$ aryl or $C_7$-$C_{11}$ aralkyl radical.

2. The process according to claim 1, wherein the reaction is carried out between 10° C. and 90° C.

3. The process according to claim 1, wherein the molar proportion of formaldehyde is between 1.5 and 2.5 moles.

4. The process according to claim 1, wherein the formaldehyde is an aqueous solution of formaldehyde having a concentration between 1% by weight and saturation.

5. The process according to claim 4, wherein the concentration of the aqueous solution of formaldehyde is from 30 to 40% in weight.

6. The process according to claim 1, wherein the reaction is carried out in an inert solvent.

7. The process according to claim 1, wherein the formaldehyde is used in non-aqueous form and the reaction is carried out in a solvent or a mixture of solvents.

8. The process of claim 7, wherein the solvent is an aprotic solvent.

9. The process of claim 7, wherein the solvent is a protic solvent.

10. A process for preparing a N-sulfomethylglycinate having the formula $HO_3S-CH_2-NH-CH_2-COOR_1$ (I), which comprises the step of reacting, at between 0° C. and 100° C., 0.95 to 3 moles of formaldehyde, 0.95 mole to saturation of sulfur dioxide, greater than 0.95 moles of an alcohol having formula $R_1OH$ (II), and 1 mole of glycine, where in formula I the $R_1$ is a linear or branched $C_1$-$C_6$ alkyl, $C_3$-$C_{12}$ cycloalkyl, $C_6$-$C_{10}$ aryl or $C_7$-$C_{11}$ aralkyl radical and $R_1$ is the same group in formulas I and II.

11. The process according to claim 10, wherein the reaction is carried out between 10° C. and 90° C.

12. The process according to claim 10, wherein the molar proportion of formaldehyde and the molar proportion of $R_1OH$ are greater than that of the glycine.

13. The process according to claim 10, wherein the molar proportion of formaldehyde is between 1.5 and 2.5 moles.

14. The process according to claim 10, wherein the molar proportion of $R_1OH$ is greater than 1.2 moles.

15. The process according to claim 10, wherein the molar proportion of $R_1OH$ is greater than 1.5 moles.

16. The process according to claim 10, wherein the molar proportion of $R_1OH$ is greater than 1.8 moles.

17. The process according to claim 10, wherein the reaction is carried out using the alcohol $R_1OH$ as a solvent.

18. The process according to claim 10, wherein the reaction is carried out using the alcohol $R_1OH$ as a solvent and using as a cosolvent an aprotic solvent.

19. The process according to claim 17, wherein $R_1OH$ is ethanol.

20. The process of claim 18, wherein $R_1OH$ is ethanol and ethanol is the solvent.

* * * * *

UNITED STATES PATENT AND TRADEMARK OFFICE
CERTIFICATE OF CORRECTION

PATENT NO. : 5,117,043
DATED : May 26, 1992
INVENTOR(S) : Botannet, et al

It is certified that error appears in the above-indentified patent and that said Letters Patent is hereby corrected as shown below:

Column 2, line 57, "R OH" should be -- $R_1OH$ --.

Column 4, line 56, "$H_2N$-N-$CH_2$-$COOR_1$" should be -- $H_2N$-$CH_2$-$COOR_1$ --.

Column 2, lines 12 - 18 and 62 - 68,

| | |
|---|---|
| glycinate | 1 mole |
| sulfur dioxide | 0.95 mole to saturation |
| formaldehyde | 0.95 to 3 moles | but preferably in a proportion greater than that of the glycinate (1.5 to 2.5 moles)" should be:

| | |
|---|---|
| glycinate | 1 mole |
| sulfur dioxide | 0.95 mole to saturation |
| formaldehyde | 0.95 to 3 moles, but preferably in a proportion greater than that of the glycinate (1.5 to 2.5 moles) |

UNITED STATES PATENT AND TRADEMARK OFFICE
CERTIFICATE OF CORRECTION

PATENT NO. : 5,117,043
DATED : May 26, 1992
INVENTOR(S) : Botannet, et al

Page 2 of 2

It is certified that error appears in the above-indentified patent and that said Letters Patent is hereby corrected as shown below:

Column 3, lines 2-8,

| $R_1OH$ | greater than 0.95 mole | but preferably in a proportion greater than that of the glycinate (greater than 1.2 moles), advantageously greater than 1.5 moles, and very advantageously greater than 1.8 moles"

should be:

| $R_1OH$ | greater than 0.95 mole, but preferably in a proportion greater than that of the glycinate (greater than 1.2 moles), advantageously greater than 1.5 moles, and very advantageously greater than 1.8 moles |

Signed and Sealed this

Twenty-fourth Day of August, 1993

Attest:

BRUCE LEHMAN

Attesting Officer

Commissioner of Patents and Trademarks